United States Patent
Mizuta et al.

(10) Patent No.: US 7,431,035 B2
(45) Date of Patent: Oct. 7, 2008

(54) RESPIRATION-SYNCHRONOUS GAS SUPPLYING DEVICE

(75) Inventors: Mamiko Mizuta, Osaka (JP); Hideo Nawata, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 416 days.

(21) Appl. No.: 10/546,047

(22) PCT Filed: Feb. 26, 2004

(86) PCT No.: PCT/JP2004/002249

§ 371 (c)(1), (2), (4) Date: Aug. 17, 2005

(87) PCT Pub. No.: WO2004/075960

PCT Pub. Date: Sep. 10, 2004

(65) Prior Publication Data

US 2006/0150972 A1 Jul. 13, 2006

(30) Foreign Application Priority Data

Feb. 28, 2003 (JP) ............................. 2003-053181

(51) Int. Cl.
*A61M 16/00* (2006.01)
(52) U.S. Cl. .............................. 128/204.23; 128/204.18
(58) Field of Classification Search ............ 128/204.17, 128/204.18, 204.21, 204.23, 204.26
See application file for complete search history.

(56) References Cited

U.S. PATENT DOCUMENTS

| 5,303,700 A | * | 4/1994 | Weismann et al. ...... 128/204.23 |
| 7,040,321 B2 | * | 5/2006 | Gobel ................... 128/207.15 |

FOREIGN PATENT DOCUMENTS

| JP | 59-008972 A | 1/1984 |
| JP | 02-088078 A | 3/1990 |
| JP | 05-184676 A | 7/1993 |
| JP | 07-096035 A | 4/1995 |
| JP | 2001-129086 A | 5/2001 |

OTHER PUBLICATIONS

International Search Report mailed Jun. 1, 2004.

* cited by examiner

*Primary Examiner*—Steven O Douglas
(74) *Attorney, Agent, or Firm*—Rader, Fishman & Grauer, PLLC

(57) ABSTRACT

As a unit which functions to prevent variations in the respiration phases of a user, erroneous recognition due to disturbances such as vibrations of the supply unit and wind, discomfort to the user due to unnecessary supply of oxygen and wasteful supply of oxygen, there is provided a respiration-synchronizing gas supply unit characterized by comprising means for recognizing the inspiration phase initial point and the expiration phase initial point, and by carrying out automatic on-off valve control with recognition means that does not recognize the next inspiration phase initial point during the time between recognition of the inspiration phase initial point and recognition of the expiration phase initial point, and between recognition of the expiration phase initial point and elapse of a predetermined time period.

10 Claims, 4 Drawing Sheets

RESPIRATION-SYNCHRONOUS GAS SUPPLYING DEVICE

TECHNICAL FIELD

The present invention relates to a respiration-synchronizing gas supply unit provided with an automatic on-off valve capable of operating in synchronization with the respiratory cycle of a user. More specifically, the invention relates to a unit for intermittently supplying a therapeutic gas such as oxygen gas to a user in synchronization with the respiratory cycle.

BACKGROUND ART

A method of increasing the oxygen utilization efficiency for oxygen obtained from oxygen cylinders or oxygen-concentrated gas obtained from oxygen concentrators has been proposed, wherein the oxygen is supplied only during inspiration and supply is interrupted during expiration, in order to achieve synchronization with the patient's respiratory cycle and thereby prevent waste of the oxygen supply during expiration (Japanese Unexamined Patent Publication No. 59-8972).

Devices which make use of this method include demand regulators provided with an automatic on-off valve and, respiration phase detection means mounted in the flow channel, which allow oxygen consumption to be conserved by opening the automatic on-off valve only during the patient's inspiration period and closing the automatic on-off valve during the expiration period. Such conservation is particularly effective for patients who carry the oxygen cylinder outdoors, as it allows the patient's use of the device to be extended approximately three-fold.

The respiration phase detection method used in the device may be a method of detecting temperature change by respiration such as described in Japanese Unexamined Patent Publication No. 59-8972, or a method of detecting pressure variation as described in Japanese Unexamined Patent Publication No. 2-88078. Such respiration phase detection means are used to recognize the initial point of the inspiration phase of the user, and a method has been proposed wherein the inspiration phase initial point is recognized when the respiratory signal falls on the inspiration phase side of a predetermined threshold value which is on the inspiration phase side of a standard value, or when the respiratory signal variation exceeds a predetermined variation threshold (Japanese Unexamined Patent Publication No. 2001-129086).

DISCLOSURE OF THE INVENTION

However, when such respiration phase detection means is used to recognize the inspiration phase initial point, it sometimes occurs that areas within the inspiration phase other than the inspiration phase initial point, or periods of variation in the respiratory signal due to vibration or wind are erroneously recognized as the inspiration phase initial point, which can result in unnecessary supply of oxygen. Such unnecessary supply of oxygen not only wastes the oxygen but also produces a feeling of discomfort for the user.

One possible method for avoiding erroneous recognition as the inspiration phase initial point areas within the inspiration phase other than the inspiration phase initial point, is a method of following each detection of the inspiration phase initial point with a fixed period without recognition of the inspiration phase initial point. However, since the respiratory cycle of a user varies from time to time and hour to hour, the method of setting a fixed period without recognizing the next inspiration phase initial point is not suitably adaptable to such variations in the respiratory cycle, and therefore areas within the inspiration phase other than the inspiration phase initial point are erroneously recognized as the inspiration phase initial point. This results in supply of oxygen when it is not needed, or conversely, the inspiration phase initial point is missed, making it impossible to supply oxygen when it is needed.

Another possible method for avoiding erroneous recognition as the inspiration phase initial point areas within the inspiration phase other than the inspiration phase initial point, is a method of recognizing the inspiration phase initial point only when the value of the respiratory signal is within a prescribed range near a standard value. However, since the respiration waveform size and rise up speed differ significantly between individual users and also vary from time to time and hour to hour for the same user, the method of recognizing the inspiration phase initial point only when the value of the respiratory signal is within a prescribed range near a standard value can result in supply of oxygen when it is not needed, in cases where the respiration waveform is small and the rise up is slow, because areas within the inspiration phase other than the inspiration phase initial point which fall within the range are erroneously recognized as the inspiration phase initial point. Conversely, the method can cause oxygen not to be supplied when needed, in cases where the respiration waveform is large and initial rise is fast, because depending on the sampling cycle of the respiratory signal, the inspiration phase initial point may fail to fall within the range and may thus be missed.

Methods also exist for avoiding erroneous recognition of variations in the respiratory signal due to vibration or wind, i.e. noise, as the inspiration phase initial point, including methods of establishing a stringent recognition standard for the inspiration phase initial point, such as a method of establishing the threshold value above the noise level in cases where the inspiration phase initial point is recognized when the respiratory signal falls on the inspiration phase side of a predetermined threshold value which is on the inspiration phase side of a standard value, or, alternatively, a method of establishing the variation threshold value above the noise level in cases where the inspiration phase is recognized when the respiratory signal variation exceeds a predetermined variation threshold. When such methods are used, however, recognition of the inspiration phase initial point may be delayed, or in some cases it may not be possible to properly recognize the inspiration phase initial point, which can lead to the problem of lack of oxygen supply when needed by the user.

As a result of much diligent research direction toward solving the problems described above, the present inventors have discovered that by providing means for recognizing the inspiration phase initial point and the expiration phase initial point of the user, and preventing recognition of the initial point of the next inspiration phase during the time between recognition of the inspiration phase initial point and recognition of the expiration phase initial point, and between recognition of the expiration phase initial point and elapse of a predetermined time period, and further by eliminating noise during recognition of the expiration phase initial point, it is possible to adapt to variations in the respiratory cycle of the user, to rapidly recognize the inspiration phase initial point of the user without errors, and to eliminate wasted release of oxygen and discomfort for the user.

Specifically, the present invention provides a respiration-synchronizing gas supply unit provided with respiratory gas generating means, conductor means having one end communicating with the generating means, having open supply means for the respiratory gas at the other end and having automatic on-off valve means between the ends, respiration phase detection means capable of detecting at least a portion of a prescribed phase of respiration and control means which controls opening and closing of the automatic on-off valve based on the respiratory signal which is the detection result from the detection means, the respiration-synchronizing gas supply unit being characterized in that the control means has recognition means which recognizes the inspiration phase initial point and the expiration phase initial point, and in that the recognition means does not recognize the initial point of the next inspiration phase during the time between recognition of the inspiration phase initial point and recognition of the expiration phase initial point, and between recognition of the expiration phase initial point and elapse of a predetermined time period.

The invention further provides a respiration-synchronizing gas supply unit characterized in that the recognition means has a standard value which is the value of the respiratory signal at the time of venting of the respiration-synchronizing gas supply unit, and recognizes as the expiration phase initial point the point at which the respiratory signal surpasses the standard value from the inspiration phase side to the expiration phase side.

The invention further provides a respiration-synchronizing gas supply unit characterized in that the recognition means has a standard value which is the value of the respiratory signal at the time of venting of the respiration-synchronizing gas supply unit, and first recognizes as the temporary expiration phase initial point the point at which the respiratory signal surpasses the standard value from the inspiration phase side to the expiration phase side, after which, if the time during which the respiratory signal is on the expiration phase side of a predetermined expiration judging threshold value on the expiration phase side of the standard value continues for at least a predetermined expiration judging time, it recognizes the first recognized temporary expiration phase initial point as the true expiration phase initial point.

The invention still further provides a respiration-synchronizing gas supply unit characterized in that the recognition means has a standard value which is the value of the respiratory signal at the time of venting of the respiration-synchronizing gas supply unit, and first recognizes as the temporary expiration phase initial point the point at which the respiratory signal surpasses the standard value from the inspiration phase side to the expiration phase side, after which, if the time during which the respiratory signal is on the inspiration phase side of the standard value or a predetermined noise judging threshold value which is on the inspiration phase side of the standard value continues for at least a predetermined noise judging time, the first recognized temporary expiration phase initial point is discarded as noise and the point at which the respiratory signal surpasses a standard value from the inspiration phase side to the expiration phase side is re-recognized as the temporary expiration phase initial point.

The invention still further provides a respiration phase detection method characterized by detecting the inspiration phase initial point and the expiration phase initial point from the respiration phase of a user, and not recognizing the next expiration phase initial point during the time between the inspiration phase initial point and the expiration phase initial point, and a predetermined time elapsed from the expiration phase initial point.

There is also provided a respiration phase detection method characterized in that the respiratory signal value at atmospheric pressure is set as the standard value and the expiration phase initial point is recognized as being the point at which the respiratory signal surpasses the standard value from the inspiration phase side to the expiration phase side, and further characterized in that the respiratory signal value at atmospheric pressure is set as the standard value, the temporary expiration phase initial point is first recognized as the point at which the respiratory signal surpasses the standard value from the inspiration phase side to the expiration phase side, after which, if the time during which the respiratory signal is on the expiration phase side of a predetermined expiration judging threshold value on the expiration phase side of the standard value continues for at least a predetermined expiration judging time, the first recognized temporary expiration phase initial point is recognized as being the true expiration phase initial point. Specifically, it is characterized in that the standard value is atmospheric pressure, in that the expiration judging threshold value is a pressure of at least 3 Pa with respect to the atmospheric pressure, and in that the expiration judging time is at least 50 msec.

There is still further provided a respiration phase detection method characterized in that the respiratory signal value at atmospheric pressure is set as the standard value, the temporary expiration phase initial point is first recognized as being the point at which the respiratory signal surpasses the standard value from the inspiration phase side to the expiration phase side, after which, if the time during which the respiratory signal is on the inspiration phase side of the standard value or a predetermined noise judging threshold value which is on the inspiration phase side of the standard value continues for at least a predetermined noise judging time, the first recognized temporary expiration phase initial point is discarded as noise and the point at which the respiratory signal surpasses a standard value from the inspiration phase side to the expiration phase side is re-recognized as the temporary expiration phase initial point; the respiration phase detection method is also characterized in that the standard value and the noise judging threshold value are atmospheric pressure and the noise judging time is a time between 100 and 200 msec.

BEST MODE FOR CARRYING OUT THE INVENTION

Figure 1:
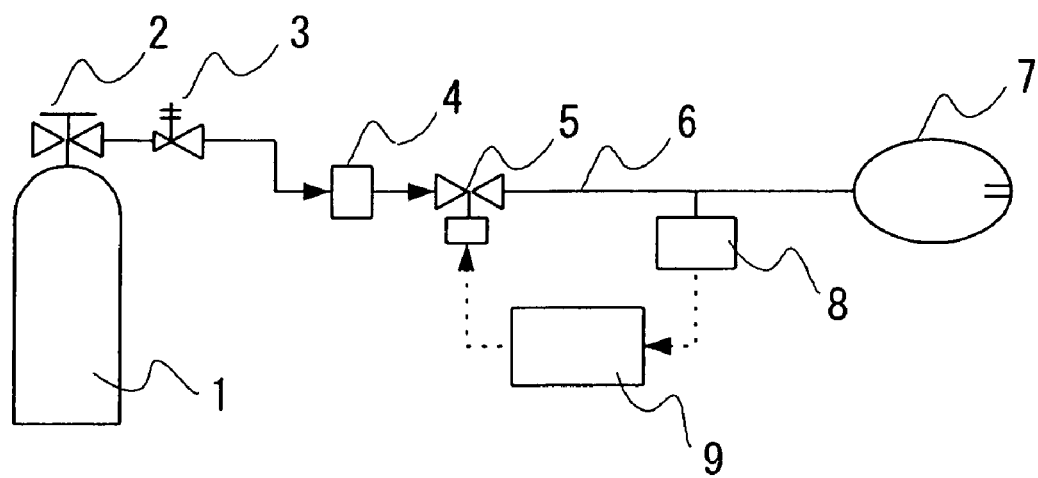
FIG. 1 is a schematic view of an embodiment of a respiration-synchronizing gas supply unit of the invention.

The respiration-synchronizing gas supply unit of the invention is a unit comprising means for recognizing the inspiration phase initial point and the expiration phase initial point of the user, wherein by preventing recognition of the initial point of the next inspiration phase during the time between recognition of the inspiration phase initial point and recognition of the expiration phase initial point, and between recognition of the expiration phase initial point and elapse of a predetermined time period afterwards, and further by eliminating noise during recognition of the expiration phase initial point, it is possible to accurately and rapidly recognize the inspiration phase initial point of the user and to open the automatic on-off valve in synchronization therewith in order to accomplish pulsed supply of a respiratory gas such as oxygen to the user.

The unit of the invention is basically composed of respiratory gas generating means, conductor means having one end communicating with the generating means, having open supply means for the respiratory gas at the other end and having automatic on-off valve means between the ends, and a demand regulator as means for controlling the opening time of the automatic on-off valve means in order to control the respiratory gas supply volume.

The respiratory gas generating means of the invention comprises pressure regulating means to regulate the pressure of the respiratory gas generating source and the gas from the generating source to the prescribed pressure, i.e. to near atmospheric pressure, and also if necessary, flow rate setting means. When a cylinder system such as an oxygen cylinder is used as the generating source, the gas from the generating source is usually supplied at a relatively high pressure of 20 MPa, and therefore pressure regulating means such as a pressure reducing valve is used to reduce the pressure to near atmospheric pressure, such as for example, 20-300 kPa and preferably 100-200 kPa.

The flow rate setting means may supply the maximum flow rate, or it may be freely set to a flow rate below the maximum, so that a constant flow with a suitable flow rate is supplied to the gas user, i.e. the patient, from the respiratory gas generating means through the conductor means.

One end of the conductor means is connected to the gas generating means, while the other end is a fixture such as a nasal canula or facial mask-which facilitates introduction of the supply gas into the body of the patient. Between the ends of the conductor means there is connected a demand regulator which is described below, and the conductor means passes by way of automatic channel on-off means of the demand regulator. It is also connected to respiration phase detection means of the demand regulator.

The control means (demand regulator) which controls the opening time of the automatic on-off valve means according to the invention opens and closes the automatic on-off valve means provided between the ends of the conductor means based on specific control conditions, in order to control the gas flow rate to the patient. The demand regulator basically consists of respiration phase detection means having the function of detecting at least a part of a prescribed phase during respiration, automatic on-off valve means and control means for control of opening and closing of the automatic on-off valve means.

As respiration phase detection means there are known (a) systems which detect temperature differences between inspiration and expiration; (b) systems wherein a sensor is provided that senses expansion and contraction in a band wound around the trunk and converts it to an electrical signal, thereby detecting movement of the trunk (respigraph); and (c) flow rate detection systems which detect changes in gas flow or pressure. Any of these may be used, although detection of the gas pressure in the canula section of the conductor end is particularly convenient.

The automatic on-off valve means may be any one which allows the gas flow in the conductor to be interrupted and circulated based on a signal from the control means. For example, there may be mentioned an air valve which opens and closes the valve by air pressure, or an electromagnetic valve which opens and closes the valve by electrical energy; however, an electromagnetic valve is particularly convenient.

The control means basically consists of means which recognizes the inspiration phase initial point and the expiration phase initial point based on the respiratory signal sent from the respiration phase detection means, means which sets the opening and closing time of the automatic on-off valve means, and on-off regulating means.

The means which recognizes the inspiration phase initial point according to the invention may be a system which recognizes the phase based on the absolute value of the respiratory signal sent from the respiration phase detection means. For example, when the respiration phase detection means used is a method of detecting the pressure of gas in the canula section, the inspiration phase initial point may be recognized as being the point where the pressure value is approximately 0 Pa.

As a different system for recognizing the inspiration phase initial point, there may be used a system which recognizes the phase based on the absolute value of the respiratory signal sent from the respiration phase detection means and on the variation in time. For example, when the respiration phase detection means used is a method of detecting the pressure of gas in the canula section, the inspiration phase initial point may be recognized as being the point where the pressure value is approximately 0 Pa and the time variation of the pressure value is less than a prescribed value, such as less than −50 Pa/sec.

The means for recognizing the expiration phase initial point according to the invention recognizes the expiration phase initial point as being the point at which the absolute value of the respiratory 'signal sent from the respiration phase detection means surpasses a standard value from the inspiration phase side to the expiration phase side, and for example, when the respiration phase detection means used is a method of detecting the pressure of gas in the canula section, the expiration phase initial point is recognized as being the point at which the pressure value surpasses 0 Pa, from the minus side to the plus side.

In order to avoid erroneous recognition due to noise during recognition of the expiration phase initial point, a temporary expiration phase initial point is first recognized without determining the expiration phase initial point, even when the respiratory signal surpasses the standard value from the inspiration phase side to the expiration phase side, and then the true expiration phase initial point is recognized when the time during which the respiratory signal is on the expiration phase side of a predetermined expiration judging threshold value on the expiration phase side of the standard value continues for at least a predetermined expiration judging time.

For example, when the respiration phase detection means used is a method of detecting the pressure of gas in the canula section, the true expiration phase initial point is recognized as being the first recognized temporary expiration phase initial point if the time that the pressure value surpasses a value on the positive side (for example, 3 Pa) continues for at least 50 msec.

Here, if the time during which the respiratory signal is on the inspiration phase side of the standard value or a predetermined noise judging threshold value which is on the inspiration phase side of the standard value continues for at least a predetermined noise judging time, before the true expiration phase initial point is recognized, i.e. while the temporary expiration phase initial point is still recognized, the first recognized temporary expiration phase initial point is discarded as noise and the point at which the respiratory signal surpasses a standard value from the inspiration phase side to the expiration phase side is re-recognized as the temporary expiration phase initial point.

For example, when the respiration phase detection means used is a method of detecting the pressure of gas in the canula section, the first recognized temporary expiration phase initial point is discarded as noise and the point at which the respiratory signal surpasses a standard value from the inspiration phase side to the expiration phase side is re-recognized as the temporary expiration phase initial point, if the time that the pressure value is below 0 Pa continues for at least 150 msec.

This makes it possible to avoid erroneously recognizing noise as the expiration phase initial point. Also, since the standard for recognition of the expiration phase initial point, i.e. the standard for recognizing the point at which the respiratory signal surpasses a standard value from the inspiration phase side to the expiration phase side as the expiration phase initial point, does not have to be stringent in order to avoid error, no delay occurs in recognition of the expiration phase initial point.

The means for recognizing the inspiration phase initial point and the expiration phase initial point according to the invention is characterized in that the next inspiration phase initial point is not recognized during the time between recognition of the inspiration phase initial point and recognition of the expiration phase initial point, and between recognition of the expiration phase initial point and elapse of a predetermined time period. Although the set time may be a prescribed time such as 200 msec, it is preferably set to match the respiratory cycle, for example, to $1/10$ of the period of the previous expiration phase. The expiration phase period may also be the average of several times.

Since the noise can be removed during recognition of the expiration phase initial point as explained above, it is possible to accurately set the period in which the inspiration phase is not recognized, and to avoid erroneously recognizing the areas in the inspiration phase other than the inspiration phase initial point, or noise, as the inspiration phase initial point. In addition, since no delay is produced in recognition of the expiration phase initial point, it is possible to rapidly set the period in which the inspiration phase initial point is not recognized, thereby allowing the next inspiration phase initial point to be recognized in adaptation to variations in the respiratory cycle. Furthermore, since the recognition standard for the inspiration phase initial point is not stringent, no delay is produced in recognition of the inspiration phase initial point as well.

Thus, it is possible to avoid erroneous recognition of areas in the inspiration phase other than the inspiration phase initial point, as well as noise, as the inspiration phase initial point, in order to adapt to variations in the respiratory cycle of the user and allow rapid recognition of the inspiration phase initial point without errors, while reducing wasted release of oxygen and discomfort for the user.

EXAMPLES

FIG. 1 is a schematic view of an embodiment of a respiratory gas supply unit of the invention. Specifically, the oxygen exiting the oxygen cylinder 1 as the respiratory gas generating means passes through a cylinder valve 2 and a pressure reduction valve 3, and then through conductor means 6 equipped with an orifice-type flow rate setting device 4 and an automatic on-off valve 5, and is emitted from a nasal canula 7 as the open supply means.

The pressure variation during respiration is converted to electrostatic capacity variation by respiration phase detection means 8 equipped with a diaphragm-type micropressure fluctuation sensor branching from the conductor means 6, and the signal is sent to control means 9.

The control means 9 converts the respiration phase data, opens the automatic on-off valve 5 at the moment in which the inspiration phase initial point is recognized, and calculates the open time of the automatic on-off valve 5, while keeping the automatic on-off valve 5 "open" during the calculating period, and subsequently closing the automatic on-off valve 5.

The next inspiration phase initial point is not recognized during the period up to recognition of the expiration phase initial point, and during the period from recognition of the expiration phase initial point up to $1/10$ of the previous expiration time, but rather, an attempt at recognizing the next inspiration phase initial point is made after that period.

Figure 2:
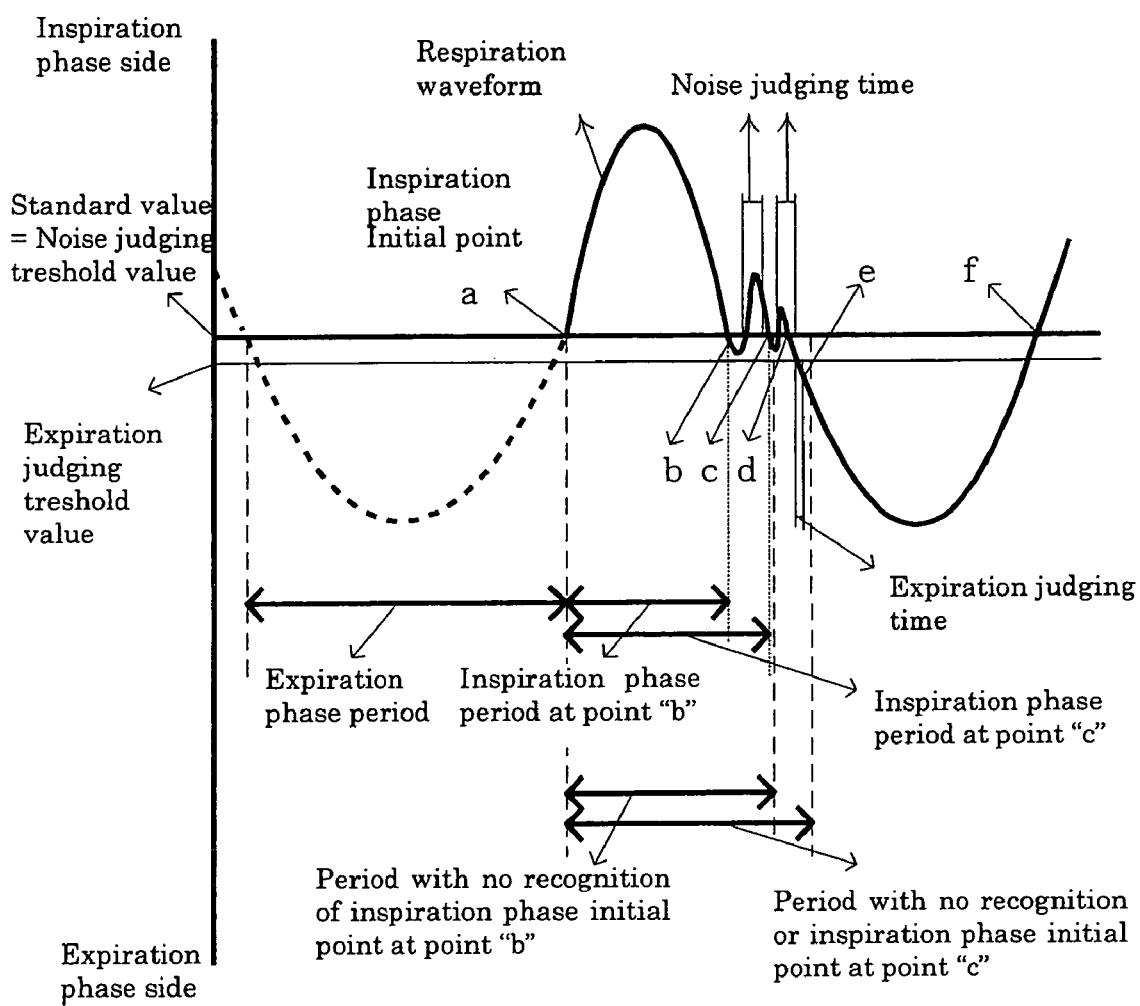
FIG. 2 is an illustration showing an example of recognizing the inspiration phase initial point and the expiration phase initial point according to the invention.

FIG. 2 is an illustration showing an example of recognizing the inspiration phase initial point and the expiration phase initial point according to the invention. First the inspiration phase initial point "a" is recognized. Since the expiration phase initial point has not yet been recognized at that point, the next inspiration phase initial point is not recognized, and therefore areas of the inspiration phase other than the inspiration phase initial point are not erroneously recognized as the inspiration phase initial point.

Next, the point "b" at which the respiratory signal surpasses the standard value from the inspiration phase to the expiration phase is recognized as the temporary expiration phase initial point. At this point, the period during which the next inspiration phase initial point is not recognized is the period equal to the temporary expiration phase initial point "b" plus $1/10$ of the previous expiration phase period, or in other words, it is the period in which the inspiration phase initial point is not recognized at point "b" in the graph.

Subsequently, the respiratory signal moves again toward the inspiration phase side without surpassing the expiration judging threshold value, and therefore the temporary expiration phase initial point "b" is not considered to be the true expiration phase initial point. Also, since this is within the period in which the inspiration phase initial point is not recognized, that area is also not recognized as the next inspiration phase initial point.

After moving toward the inspiration phase side, the time during which it is on the inspiration phase side of the noise judging threshold value, which is the same value as the standard value in this example, is longer than the noise judging time, and therefore the temporary expiration phase initial point "b" is discarded and the point "c" from the inspiration phase side to the expiration phase side is re-recognized as the temporary expiration phase initial point.

At this point, the period during which the next inspiration phase initial point is not recognized is the period equal to the temporary expiration phase initial point "c" plus $1/10$ of the previous expiration phase period, or in other words, it is the period in which the inspiration phase initial point is not recognized at point "c" in the graph, and thus the temporary expiration phase initial point is prolonged by the difference between "b" and "c".

Subsequently, the signal moves again toward the inspiration phase side, but because the period in which the inspiration phase initial point is not recognized has been prolonged, that portion is not recognized as the next inspiration phase initial point. In addition, since in this case the time on the inspiration phase side of the noise judging threshold value does not reach the noise judging time, the temporarily recognized expiration phase initial point "c" is not discarded, and therefore point "d" which has again moved toward the expiration phase side is not re-recognized as the expiration phase initial point, leaving "c" to be recognized as the temporary expiration phase initial point.

Next, the temporary expiration phase initial point "c" is recognized as the true expiration phase initial point at time point "e" where the time on the expiration phase side of the expiration judging threshold value is longer than the expiration judging time.

The next inspiration phase initial point is recognized as being point "f" at which the respiratory signal has moved toward the inspiration phase side, after the period in which the inspiration phase initial point is not recognized, i.e. the period which represents the period in which the inspiration phase initial point is not recognized at point "c" in the graph.

Figure 3:
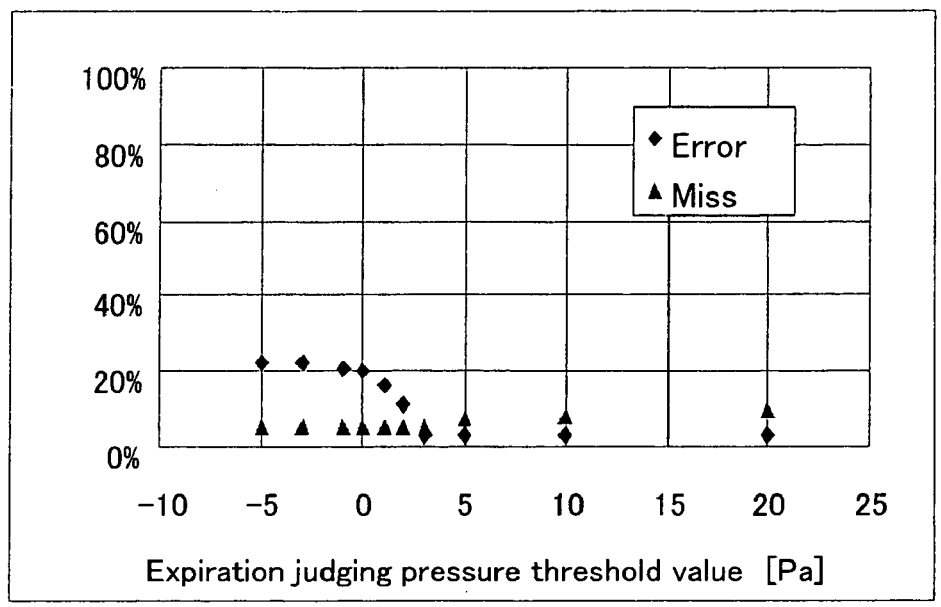
FIG. 3 is a graph showing the ratio of erroneous detections and detection misses with respect to expiration judging pressure threshold value for the respiration waveform of a user.

The accurate value for the expiration judging threshold value was determined from the proportion of erroneous detections, i.e. cases where an inspiration initial point was recognized in the absence of an actual inspiration initial point, and the proportion of detection misses, i.e. cases where an inspiration initial point was missed among 330 respiratory cycles, based on the respiratory pressure waveform as shown in FIG. 3. It is apparent that the proportion of erroneous detections increases sharply at pressure below 3 Pa. On the other hand, although the proportion of detection misses is virtually unchanged, it tends to increase slightly with increasing pressure. As a result, the expiration judging pressure threshold value is preferably set to be 3 Pa or greater, more preferably in the range of 3-10 Pa, and even more preferably in the range of 3-5 Pa.

Figure 4:
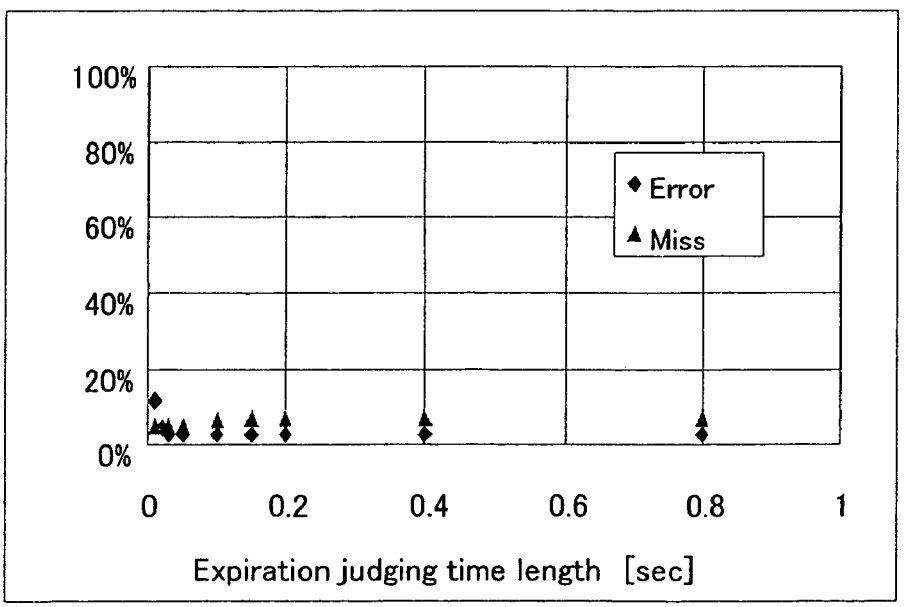
FIG. 4 is a graph showing the ratio of erroneous detections and detection misses with respect to expiration judging time length for the respiration waveform of a user.

In the same manner as above, the accurate value for the length of the expiration judging time was determined from the proportion of erroneous detections and detection misses among 330 respiratory cycles, based on the respiratory pressure waveform of the patient as shown in FIG. 4. As a result, the proportion of erroneous detections increased up to 50 msec, and the detection misses did not affect the judging time. Thus, the expiration judging time is preferably set to be at least 50 msec.

Figure 5:
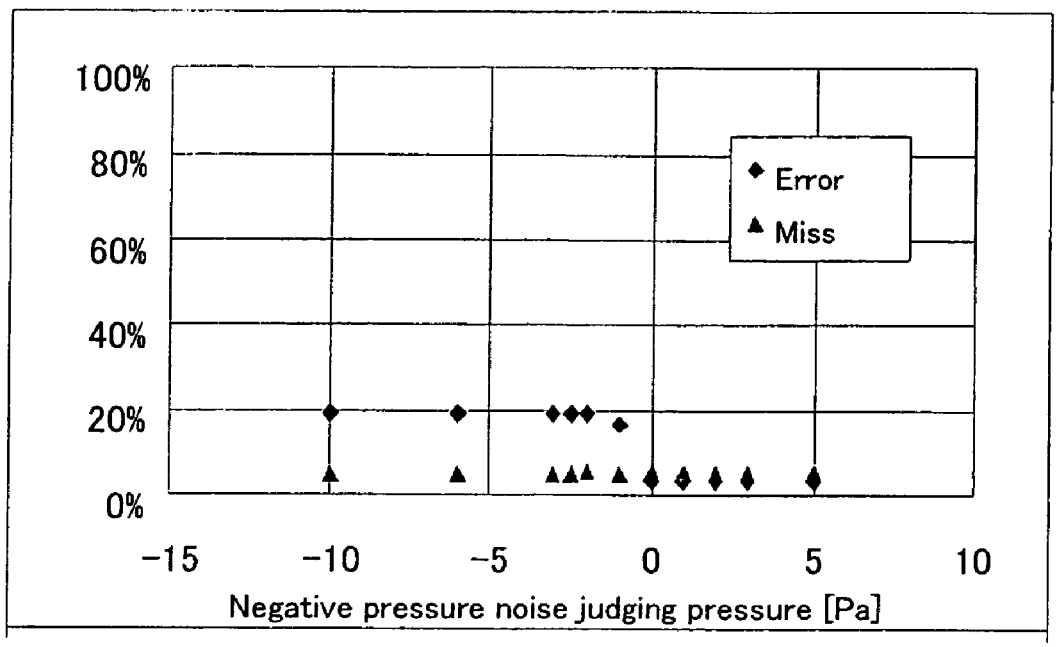
FIG. 5 is a graph showing the ratio of erroneous detections and detection misses with respect to noise judging pressure value for the respiration waveform of a user.

On the other hand, when the noise judging pressure value was below atmospheric pressure as the standard pressure, the proportion of erroneous detections increased, as shown in FIG. 5. Thus, the noise judging pressure is preferably set to be the same as atmospheric pressure, as the standard pressure, or else a pressure above atmospheric pressure.

Figure 6:
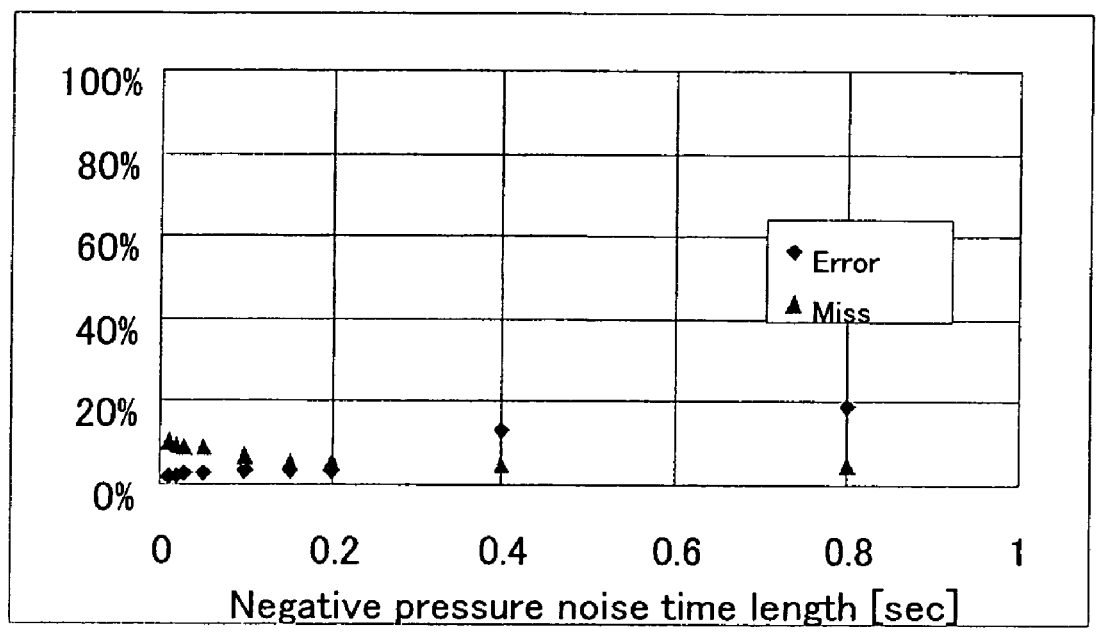
FIG. 6 is a graph showing the ratio of erroneous detections and detection misses with respect to noise judging time length for the respiration waveform of a user.

For the noise judging time as well, the accurate value was determined from the proportion of erroneous detections and detection misses among 330 respiratory cycles, based on the respiratory pressure waveform of the patient as shown in FIG. 6. As a result, the proportion of detection misses increased up to 50 msec, while the proportion of erroneous detections increased at above 400 msec. Therefore, the noise judging time is preferably set to be within the range of 100-200 msec.

As an example there may be proposed an expiration judging threshold value of +3 Pa over atmospheric pressure, an expiration judging time of 50 msec, a noise judging pressure of atmospheric pressure and a noise judging time of 150 msec, but other suitable combinations within the ranges specified above may be used.

Effect of the Invention

The respiration-synchronizing gas supply unit of the invention adapts to variations in the respiratory cycle of a user without erroneously recognizing the areas in the inspiration phase other than the inspiration phase initial point, or noise, as the inspiration phase initial point, in order to allow rapid and error-free recognition of the inspiration phase initial points, thereby reducing wasted release of oxygen and discomfort for the user.

The invention claimed is:

1. A respiration-synchronizing gas supply unit comprising:
respiratory gas generating means;
conductor means having one end communicating with said generating means, having open supply means for said respiratory gas at the other end and having automatic on-off valve means between the ends; and
respiration phase detection means for detecting at least a portion of a prescribed phase of respiration and control means which controls opening and closing of said automatic on-off valve means based on a respiratory signal which is a detection result from said detection means,
wherein said control means has recognition means which recognizes the inspiration phase initial point and the expiration phase initial point,
said recognition means does not recognize the initial point of the next inspiration phase during the time between recognition of the inspiration phase initial point and recognition of the expiration phase initial point, and between recognition of the expiration phase initial point and elapse of a predetermined time period, and
wherein said recognition means has a standard value which is the value of the respiratory signal at the time of venting of said respiration-synchronizing gas supply unit, and recognizes as the expiration phase initial point the point at which the respiratory signal surpasses said standard value from an inspiration phase side to an expiration phase side.

2. A respiration-synchronizing gas supply unit comprising:
respiratory gas generating means;
conductor means having one end communicating with said generating means, having open supply means for said respiratory gas at the other end and having automatic on-off valve means between the ends; and
respiration phase detection means for detecting at least a portion of a prescribed phase of respiration and control means which controls opening and closing of said automatic on-off valve means based on a respiratory signal which is a detection result from said detection means,
wherein said control means has recognition means which recognizes the inspiration phase initial point and the expiration phase initial point, said recognition means does not recognize the initial point of the next inspration phase during the time between recognition of the inspiration phase initial point and recognition of the expiration phase initial point, and between recognition of the expiration phase initial point and elapse of a predetermined time period, and
wherein the recognition means has a standard value which is the value of the respiratory signal at the time of venting of said respiration-synchronizing gas supply unit, and first recognizes as a temporary expiration phase initial point the point at which the respiratory signal surpasses said standard value from an inspiration phase side to an expiration phase side, after which, if the time during which the respiratory signal is on the expiration phase side of a predetermined expiration judging threshold value on the expiration phase side of the standard value continues for at least a predetermined expiration judging time, it recognizes the first recognized temporary expiration phase initial point as a true expiration phase initial point.

3. A respiration-synchronizing gas supply unit according to claim 1 or 2, wherein the recognition means has a standard value which is the value of the respiratory signal at the time of venting of said respiration-synchronizing gas supply unit, and first recognizes as the temporary expiration phase initial point the point at which the respiratory signal surpasses said standard value from the inspiration phase side to the expiration phase side, after which, if the time during which the respiratory signal is on the inspiration phase side of said standard value or a predetermined noise judging threshold value which is on the inspiration phase side of said standard value continues for at least a predetermined noise judging time, the first recognized temporary expiration phase initial point is discarded as noise and the point at which the respiratory signal surpasses a standard value from the inspiration phase side to the expiration phase side is re-recognized as the temporary expiration phase initial point.

4. A respiration phase detection method comprising a step of:
   detecting the inspiration phase initial point and the expiration phase initial point from the respiration phase of a user,
   not recognizing the next inspiration phase initial point during the time between the inspiration phase initial point and the expiration phase initial point, and
   a predetermined time elapsed from the expiration phase initial point,
   wherein a respiratory signal value at atmospheric pressure is set as a standard value and the expiration phase initial point is recognized as being the point at which the respiratory signal surpasses said standard value from an inspiration phase side to an expiration phase side.

5. A respiration phase detection method comprising a step of:
   detecting the inspiration phase initial point and the expiration phase initial point from the respiration phase of a user,
   not recognizing the next inspiration phase initial point during the time between the inspiration phase initial point and the expiration phase initial point, and
   a predetermined time elapsed from the expiration phase initial point
   wherein a respiratory signal value at atmospheric pressure is set as a standard value, a temporary expiration phase initial point is first recognized as the point at which the respiratory signal surpasses said standard value from the inspiration phase side to the expiration phase side, after which, if the time during which the respiratory signal is on an expiration phase side of a predetermined expiration judging threshold value on the expiration phase side of said standard value continues for at least a predetermined expiration judging time, a first recognized temporary expiration phase initial point is recognized as being a true expiration phase initial point.

6. A respiration phase detection method according to claim 5, wherein said standard value is atmospheric pressure, and in that said expiration judging threshold value is a pressure of at least 3 Pa with respect to said atmospheric pressure.

7. A respiration phase detection method according to claim 4 or 5, wherein said expiration judging time is at least 50 msec.

8. A respiration phase detection method according to claim 4 or 5, wherein the respiratory signal value at atmospheric pressure is set as the standard value, the temporary expiration phase initial point is first recognized as being the point at which the respiratory signal surpasses said standard value from the inspiration phase side to the expiration phase side, after which, if the time during which the respiratory signal is on the inspiration phase side of said standard value or a predetermined noise judging threshold value which is on the inspiration phase side of said standard value continues for at least a predetermined noise judging time, the first recognized temporary expiration phase initial point is discarded as noise and the point at which the respiratory signal surpasses a standard value from the inspiration phase side to the expiration phase side is re-recognized as the temporary expiration phase initial point.

9. A respiration phase detection method according to claim 8, wherein said standard value and said noise judging threshold value are atmospheric pressure and said noise judging time is a time between 100 and 200 msec.

10. A respiration-synchronizing gas supply unit comprising:
   a respiratory gas generator;
   a conductor having one end communicating with said generator, having open supply unit for said respiratory gas at the other end and having automatic on-off valve between the ends; and
   a respiration phase detector for detecting at least a portion of a prescribed phase of respiration and controller which controls opening and closing of said automatic on-off valve means based on a respiratory signal which is a detection result from said detector,
   wherein said controller has a recognition feature which recognizes the inspiration phase initial point and the expiration phase initial point,
   said recognition feature does not recognize the initial point of the next inspiration phase during the time between recognition of the inspiration phase initial point and recognition of the expiration phase initial point, and between recognition of the expiration phase initial point and elapse of a predetermined time period, and
   said recognition feature has a standard value which is the value of the respiratory signal at the time of venting of said respiration-synchronizing gas supply unit, and recognizes as the expiration phase initial point the point at which the respiratory signal surpasses said standard value from an inspiration phase side to an expiration phase side.

* * * * *